United States Patent [19]

Weinberger et al.

[11] Patent Number: Plant 6,009

[45] Date of Patent: Sep. 8, 1987

[54] GRAPEVINE, SUGRASIX

[76] Inventors: John H. Weinberger, 6111 E. Lyell, Fresno, Calif. 93727; Timothy P. Sheehan, 8701 N. Highway 41, No. 25, Fresno, Calif. 93710

[21] Appl. No.: 787,459

[22] Filed: Oct. 15, 1985

[51] Int. Cl.[4] ..... A01H 5/00

[52] U.S. Cl. ..... Plt./47

[58] Field of Search ..... Plt./47

*Primary Examiner*—James R. Feyrer

*Attorney, Agent, or Firm*—Worrel & Worrel

[57] ABSTRACT

The grapevine is particularly characterized by its grapes which are generally similar in date or ripening to those of the Flame Seedless Grapevine (unpatented), having the physical characteristics of being seedless, similar to the Flame Seedless but which is distinguished therefrom by producing smaller clusters of grapes which are nearly Red-black in color, in contrast to the red color of the Flame Seedless variety of grapevine (unpatented).

1 Drawing Figure

BACKGROUND OF THE NEW VARIETY

The present invention relates to a new and distinct variety of grapevine, to be known varietally as the Sugrasix Grapevine, and more particularly to a grapevine which produces grapes which are generally similar when ripe to the grapes of the Flame Seedless Grapevine (unpatented), but which differs therefrom in producing clusters or bunches of grapes which are smaller in size than those of the Flame Seedless Grapevine, and bears grapes which are a dark red-black in color, in contrast to the reddish color fruit which is characteristically produced by the Flame Seedless Grapevine.

A substantial portion of the applicants' professional efforts are devoted to the creation of new and distinct varieties of grapevines. The present variety resulted from the applicants' efforts to produce a new and distinctive variety of seedless grape. Employees under the direction of Superior Farming Company, of Bakersfield, Calif., have regularly selected grapevines having desired characteristics, and have cross-pollinated these selected grapevines to try and produce progeny of improved characteristics. For example, in the creation of the instant variety of grapevine, an object of the present invention was to produce a seedless grape, which matured relatively early in the season.

ORIGIN AND ASEXUAL REPRODUCTION OF THE NEW VARIETY

An unknown employee, under the direction of Superior Farming Company of Bakersfield, Calif., cross-pollinated a selection from a Ribier variety of grapevine (unpatented), and a Superior Seedless grapevine (U.S. Plant Pat. No. 3,106) at a test plot located at the Superior Farming Company Ranch located near Wasco, Kern County, Calif., in 1977. The pollination of the Ribier flower, with pollen of Superior Seedless grapes, produced a resultant progeny that were grown to an extent sufficient to determine that their characteristics were desirable. The subject variety was discovered and subsequently selected by the applicants, John H. Weinberger and Timothy P. Sheehan for its noteworthy characteristics and asexually reproduced by each of them, by cuttings that were made in 1980. The characteristics of the grapevines resulting from this asexual reproduction were identical to those of the original grapevine.

BRIEF DESCRIPTION OF THE DRAWING

The accompanying drawing is a color photograph of a bunch of grapes of the subject variety, several leaves are displayed showing their dorsal coloration, and a typical section of the vine of the subject variety is displayed.

DETAILED DESCRIPTION

Referring more particularly to the pomological details of the new and distinct variety of grapevine, the following has been observed under the ecological conditions prevailing at the applicant's designated ranch near Wasco, Kern County, Calif.

All major color code designations are by reference to the Munsell Limit Color Cascade. Common color names are also used in several instances.

VINE

Vigor: Average.

Form: Upright, and dense, depending upon pruning practices.

Productivity: Productive.

Trunk: Medium in size and shape.

Bark: Shreddy.

Canes: Medium in length, average in number.

- *Thickness.*—Average.
- *Color.*—Green, changing to Light Brown when mature.
- *Shape.*—Straight.

Nodes:

- *Shape.*—Angular.

Internodes:

- *Length.*—Medium.

Tendrils: Intermittent.

- *Thickness.*—Slender.
- *Length.*—Medium.
- *Position.*—Bifurcated.
- *Texture.*—Smooth.

Flowers:

- *Date of bloom.*—Average as compared to other varieties.

LEAVES

Size: Medium.
Shape: Roundish.
*Thickness.*—Average.
*Color.*—Dorsal surface — dull, Medium Green (MCC 22-14).
*Texture.*—Dorsal surface — smooth.
*Color.*—Ventral surface — Pale Green (MCC 24-13).
*Texture.*—Ventral surface — hairy.
*Lobes.*—Number — five.
*Terminal lobe.*—Obtuse.
*Petiolar sinus.*—Medium in depth and width.
*Basal sinus.*—Medium in depth and width.
*Lateral sinus.*—Deep in depth, narrow in width.
*Margin.*—Serrate.
*Teeth.*—Medium in depth and width.

FRUIT

Maturity when described:
*Date of ripening for harvesting.*—Approximately July 26; ripening date is early as compared to other varieties.
Keeping quality: Good.
Shipping quality: Good.
Cluster:
*Size.*—Average; average in length; medium in width; tapering in appearance; regular; double-shouldered; medium in density.
*Peduncle.*—Average in length; medium in width.
*Pedicel.*—Average in length; medium in width.
Brush: Short in length.
*Color.*—Yellow.
Berry: Medium adherent; average in size.

*Shape.*—Uniform and roundish.
*Color.*—Deep Red-Black (MCC 45-15).
Bloom: Average in amount.
Skin: Medium in thickness and toughness; skin adheres to the pulp.
Flesh:
*Color.*—Greenish and translucent.
*Texture.*—Average; tender; juicy; sweet; and clear.
Quality: Excellent.
Seeds:
*Number of seeds.*—Seedless, occasional seed traces may be present, but no mature seeds have been found.
Use: Fresh market.

Although the new variety of grapevine possesses the described characteristics as a result of the growing conditions prevailing in the San Joaquin Valley of Central California, it is to be understood that conditions of the usual magnitude in characteristics incident to growing conditions, fertilization, pruning and pest control are to be expected.

Having thus described and illustrated our new variety of grapevine, we claim:

1. A new and distinct variety of grapevine to be known as Sugrasix and the parts thereof, substantially as illustrated and described, characterized principally by its production of grapes which mature in the same season of ripening as the Flame Seedless Grape (unpatented) which it most closely resembles, but from which it is distinguished by producing clusters of seedless grapes which are nearly Red-black in color in contrast to the reddish color characteristic of the Flame Seedless Grapevine variety (unpatented).

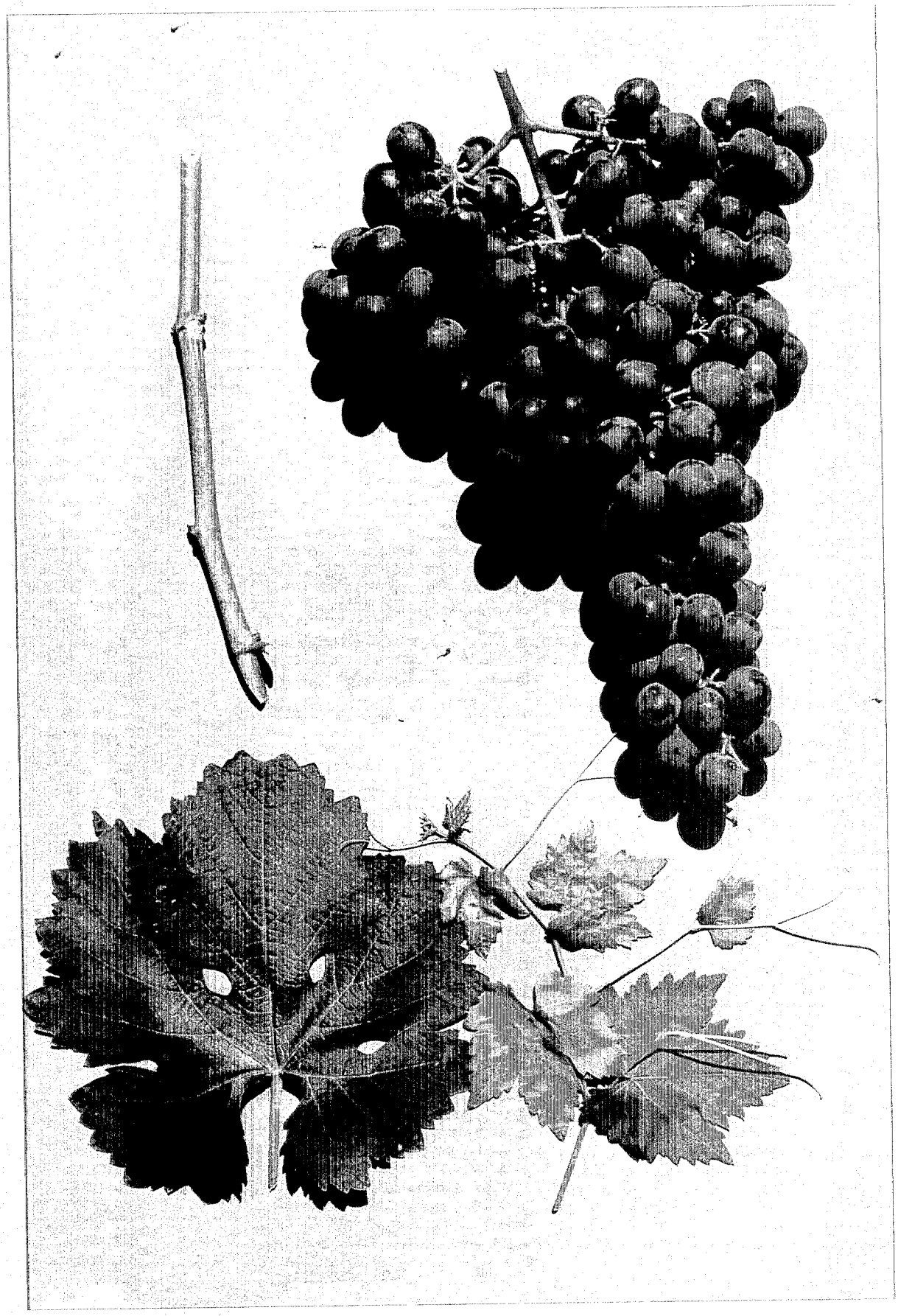

* * * * *